United States Patent [19]

Imai et al.

[11] 4,339,617

[45] Jul. 13, 1982

[54] HYDRATION OF OLEFINS IN THE PRESENCE OF A CORROSION INHIBITOR

[75] Inventors: Tamotsu Imai, Mount Prospect; Robert J. Schmidt, Hoffman Estates, both of Ill.

[73] Assignee: UOP Inc., Des Plaines, Ill.

[21] Appl. No.: 241,868

[22] Filed: Mar. 9, 1981

Related U.S. Application Data

[63] Continuation-in-part of Ser. No. 135,743, Mar. 31, 1980, abandoned.

[51] Int. Cl.$^3$ ............................................. C07C 29/04
[52] U.S. Cl. .................................. 568/899; 568/895; 568/897; 568/898; 568/900; 568/901
[58] Field of Search ................................ 568/895–901

[56] References Cited

U.S. PATENT DOCUMENTS

| | | | |
|---|---|---|---|
| 2,020,674 | 11/1935 | Dreyfus | 568/901 |
| 2,045,842 | 6/1936 | Dreyfus | 260/156 |
| 2,050,442 | 8/1936 | Metzger | 260/156 |
| 2,050,444 | 8/1936 | Metzger | 260/156 |
| 2,051,046 | 8/1936 | Horsley | 568/901 |
| 2,106,521 | 1/1938 | Deanesly | 260/99.12 |
| 2,891,999 | 6/1959 | Langer | 568/901 |
| 3,328,469 | 6/1967 | Spector et al. | 568/900 |
| 3,996,298 | 12/1976 | Izumi et al. | 568/901 |
| 4,060,564 | 11/1977 | Kanemaru et al. | 568/898 |
| 4,236,034 | 11/1980 | Aoshima et al. | 568/897 |

FOREIGN PATENT DOCUMENTS

| | | | |
|---|---|---|---|
| 368935 | 8/1934 | United Kingdom. | |
| 2024812 | 1/1980 | United Kingdom | 568/900 |

*Primary Examiner*—Joseph E. Evans
*Attorney, Agent, or Firm*—James R. Hoatson, Jr.; Raymond H. Nelson; William H. Page, II

[57] ABSTRACT

Olefinic hydrocarbons may be hydrated to form corresponding alcohols by treating said olefins with water in the presence of an acidic compound which acts as a catalyst, said hydration reaction being effected at a temperature in the range of from about 100° to about 300° C. and a pressure in the range of from about 1 to about 100 atmospheres. In addition, the reaction medium also contains a salt of a metal selected from the group consisting of magnesium, barium, beryllium and radium, said metal salts suppressing the corrosive nature of the acid catalyst and thus permitting the reaction to be effected in normal metal reactors.

15 Claims, No Drawings

HYDRATION OF OLEFINS IN THE PRESENCE OF A CORROSION INHIBITOR

CROSS-REFERENCE TO RELATED APPLICATIONS

This application is a continuation-in-part of our co-pending application Ser. No. 135,743 filed Mar. 31, 1980 and now abandoned.

BACKGROUND OF THE INVENTION

The manufacture or preparation of alcohols utilizing an olefinic hydrocarbon is known in the art. For example, U.S. Pat. No. 2,106,521 discloses a method for manufacturing oxygen-containing compounds such as alcohols, ethers, esters, etc. by treating an olefinic hydrocarbon with an acid-acting media such as sulfuric acid, phosphoric acid, pyrophosphoric acid, or with aqueous solutions of suspensions of acid-acting salts such as sodium bisulfate. The patent also teaches that the concentration in which such acid-acting media may be used will depend on the nature of the acid-acting compound and the olefinic hydrocarbon which is to be treated, concentrations of acid ranging from about 40% to about 100%. Likewise, U.S. Pat. No. 2,045,842 discloses a process for the hydration of olefins and particularly ethylene to prepare ethyl alcohol. The reference teaches that the process is effected in the presence of dilute solutions of an acid or other hydration catalysts and, in addition to these compounds, the reaction medium may contain metals, salts, or other substances capable of promoting the adsorption of ethylene. These ethylene adsorption compounds could include silver, copper, silver sulfate, calcium sulfate, lead sulfate, iron sulfate, etc., the compounds being conveniently employed in an amount of between 0.5 to 4% of the solution; also other proportions may be employed. U.S. Pat. Nos. 2,050,442 and 2,050,444 relate to a method for preparing ethyl alcohol and isopropyl alcohol respectively. In the former, ethylene is prepared by placing a mixture of ethylene and steam into intimate contact with a dilute sulfuric acid solution and also teaches that silver or silver sulfate, as well as lithium sulfate, may be used as a promoter to enable the process to be carried out at a lower temperature than has heretofore been used. The latter patent is similar in nature to the patent just discussed, but treats propylene with water vapor in the presence of a sulfuric acid catalyst and in the presence, if so desired, of silver, silver sulfate, or lithium sulfate as a promoter. Another prior patent which teaches the production of aliphatic alcohols is British specification No. 368,935 which teaches the treatment of ethylene with a catalyst such as sodium acid sulfate, potassium acid sulfate, aluminum acid sulfate, and other sulfates having an acid property.

As will hereinafter be shown in greater detail, it has now been discovered that alcohols may be produced by the hydration of olefins in the presence of an acidic catalyst and also in the presence of a corrosion inhibitor whereby it is possible to prepare the desired alcohols utilizing reaction equipment which is relatively inexpensive in nature as an equipment cost and, due to the presence of the corrosion inhibitor, will not require either protective maintenance or replacement as would be necessary when effecting the process in the absence of such corrosion inhibitor compounds.

SUMMARY OF THE INVENTION

This invention relates to a process for the hydration of olefinic hydrocarbons. More specifically, the invention is concerned with a process for treating olefinic hydrocarbons with water in the presence of a catalyst comprising an acidic compound and a salt of a metal selected from Group IIA of the Periodic Table.

Alcohols are important basic chemicals which find a wide variety of uses in industry. For example, ethyl alcohol is a basic chemical which is used as a solvent and in the manufacture of intermediates, dyes, synthetic drugs, synthetic rubbers, detergents, cleaning source, surface coatings, cosmetics, pharmaceuticals, beverages, etc. Isopropyl alcohol is used in the manufacture of acetone which, in turn, is a source of acetic anhydride, diacetone alcohol, methyl isobutyl ketone and other derivatives. It is also used as a solvent for essential oils, gums, resins; as a latent solvent for cellulose derivatives; as an antistalling agent in liquid fuels or as an intermediate in the manufacture of pharmaceuticals, perfumes, lacquers, etc. Likewise, dodecyl alcohol, which is also known as lauryl alcohol, is used in the manufacture of synthetic detergents, lube additives, pharmaceuticals, rubber, textiles and perfumes. Tetradecanol, which is also known as myristyl alcohol, is used in organic synthesis, as a plasticizer, antifoam agent, as a perfume fixitive for soaps and cosmetics as well as other uses. As will hereinafter be set forth in greater detail, it has now been discovered that the preparation of these alcohols may be attained by treating or hydrating an olefinic hydrocarbon with water in the presence of certain catalytic compositions of matter.

It is therefore an object of this invention to provide a process for the hydration of olefinic hydrocarbons.

A further object of this invention is found in process for the hydration of olefinic hydrocarbons utilizing a novel catalyst system.

In one aspect, an embodiment of this invention resides in a process for the hydration of an olefinic hydrocarbon which comprises reacting said olefinic hydrocarbon in the presence of a catalyst comprising an acidic compound at hydration conditions and recovering the resultant alcohol, the improvement which comprises effecting the hydration reaction in the added presence of a corrosion inhibitor selected from the group consisting of the salts of magnesium, barium, beryllium and radium.

A specific embodiment of this invention is found in a process for the hydration of an organic hydrocarbon which comprises reacting propylene with water in the presence of a catalyst comprising sulfuric acid in the added presence of magnesium sulfate at a temperature in the range of from about 100° to about 300° C. and a pressure in the range of from about 1 to about 300 atmospheres, and recovering the resultant isopropyl alcohol.

Other objects and embodiments will be found in the following further detailed description of the present invention.

DETAILED DESCRIPTION OF THE INVENTION

As hereinbefore set forth, the present invention is concerned with a process for the hydration of olefins in which olefinic hydrocarbons are reacted with water in the presence of an acidic compound which acts as a catalyst and in the added presence of a corrosion inhibitor which is selected from the group consisting of salts of magnesium, barium, beryllium and radium. It is well known that various acidic compounds, including both inorganic and organic acids, may be used to catalyze the hydration of olefins to form the corresponding alcohols. However, the use of acidic catalysts has an inherent disadvantage in that the acid catalysts are highly corrosive in nature, attacking the metallic surfaces of the various reactors in which the hydration is effected. This property of the acid catalysts is detrimental to the process inasmuch as it is not possible to use conventional types of reactors and thus necessitates the use of relatively expensive equipment which is highly resistant to acid corrosion. In addition to using types of materials which are relatively expensive and difficult to fabricate, a relatively large amount of time is lost in producing alcohols when the corroded equipment needs to be replaced, thus adding to the final expense of the finished product, said expense including the replacement of the equipment as well as downtime in the process line.

It has now been discovered that the corrosive nature of the various catalysts which are employed may be minimized or suppressed to a great degree by effecting the process in the presence of a salt of a metal selected from magnesium, barium, beryllium and radium. The presence of these metal salts is beneficial, not only from the standpoint of suppressing the corrosion problems relating to the equipment, but also of maintaining the high catalytic activity of the acid catalyst. This benefit will be set forth in greater detail in the examples at the end of the specification.

Examples of olefinic hydrocarbons which may be employed as the starting materials in the process of this invention will comprise olefins containing from 2 to about 20 carbon atoms or more and preferably those containing from 2 to about 5 carbon atoms. Specific examples of these olefinic hydrocarbons will include ethylene, propylene, butene-1, butene-2, isobutylene, pentene-1, pentene-2, hexene-1, hexene-2, hexene-3, the isomeric heptenes, octenes, nonenes, decenes, hendecenes, dodecenes, tridecenes, tetradecenes, pentadecenes, hexadecenes, heptadecenes, octadecenes, nonadecenes, eicosenes, etc. The aforesaid olefinic hydrocarbons are hydrated by treatment with water in which said water is present in a mole ratio of from about 2:1 up to about 60:1 moles of water per mole of olefin. The reaction conditions which are employed to effect the hydration will include elevated temperatures in the range of from about 100° to about 300° C. or more and pressures within a range of from about 1 to about 300 atmospheres. It is contemplated that superatmospheric pressures which are employed will be afforded by the autogenous pressure of the olefinic hydrocarbon, if in gaseous form, or by the introduction of a substantially inert gas such as nitrogen, helium, argon, etc., into the reaction zone.

Acidic catalysts which are employed to effect the reaction of the present invention will comprise aqueous acids and may be either organic or inorganic in nature. Some specific examples of acidic catalysts which may be employed will include mineral acids such as sulfuric acid, hydrochloric acid, nitric acid, phosphoric acid, etc., heteropoly inorganic acids such as 12-tungstosilicic acid, 12-tungstophosphoric acid, 12-molybdophosphoric acid, 12-tungstogermanic acid, 10-tungsto-2-vanadophosphoric acid, etc., organic sulfonic acids such as benzenesulfonic acid, toluenesulfonic acid, methylsulfonic acid, ethylsulfonic acid, etc., superacids such as fluorosulfonic acid, trifluoromethanesulfonic acid, etc. It is to be understood that the aforementioned acids are only representative of the type of catalysts which may be employed and that the present invention is not necessarily limited thereto.

As hereinbefore set forth, the hydration reaction of the present invention, besides being effected in the presence of an acidic catalyst, is also effected in the presence of a corrosion inhibitor comprising a salt of magnesium, barium, beryllium and radium. Some specific examples of these salts which may be employed will include magnesium sulfate, magnesium nitrate, magnesium chloride, magnesium bromide, magnesium iodide, magnesium carbonate, barium sulfate, barium nitrate, barium chloride, barium bromide, barium iodide, barium carbonate, beryllium sulfate, beryllium nitrate, beryllium chloride, beryllium bromide, beryllium iodide, beryllium carbonate, radium sulfate, radium nitrate, radium chloride, radium bromide, radium iodide, radium carbonate, etc. It is to be understood that the aforementioned salts are only representative of the class of corrosion inhibitors which may be employed and that the present invention is not necessarily limited thereto.

The process of this invention may be effected in any suitable manner and may comprise either a batch or continuous type of operation. For example, when a batch type of operation is to be employed, the desired quantity of water is placed in an appropriate apparatus which may be of the pressure-resistant type such as an autoclave. In addition, an aqueous acid catalyst and the metal salt of the type hereinbefore set forth in greater detail are also placed in the apparatus. The apparatus is then sealed and the olefinic hydrocarbon, if in gaseous form, is pressed in until the desired operating pressure has been attained. Thereafter, the apparatus and contents thereof are heated to the predetermined operating temperature and maintained thereat for a period of time which may range from about 0.5 up to about 10 hours or more in duration, the residence time for the reaction being dependent upon the operating parameters of temperature and pressure as well as the olefinic hydrocarbon which is to undergo hydration. In the event that the olefinic hydrocarbon is in liquid form, it is also charged to the reactor prior to sealing the apparatus. After charging the olefinic hydrocarbon to the vessel and sealing the same, the desired operating pressure is attained by charging an inert gas thereto. After completing the reaction, heating is discontinued and after the apparatus and contents thereof have returned to room temperature, the excess pressure is discharged and the reactor is opened. The reaction mixture is recovered from the vessel and subjected to conventional means of separation such as fractional distillation, fractional crystallization, decantation, etc., whereby the desired alcohol is separated from the catalyst, water and any unreacted olefinic hydrocarbon, and recovered.

It is also contemplated within the scope of this invention that a continuous manner of operation may be employed to produce the desired product. When such a type of operation is employed, the olefinic hydrocarbon comprising the feed stock is continuously charged to a reaction vessel which contains the acid catalyst, water and metal salt of the type hereinbefore set forth. If so desired, the latter three components of the reaction mixture may also be continuously charged to the reactor through separate lines or as an admixture thereof. After passage through the vessel, which is maintained at the proper operating conditions of temperature and pressure, the reactor effluent is continuously withdrawn and subjected to conventional means of separation whereby the desired alcohol is recovered, while any unreacted olefin, water, catalyst and metal salt are recycled to the reaction zone to form a portion of the feedstock.

The following examples are given for purposes of illustrating the process of this invention. However, it is to be understood that these examples are merely illustrative of the process of this invention and that this process is not necessarily limited thereto.

EXAMPLE I

To illustrate the corrosive nature of an acidic catalyst per se, a piece of stainless steel 316 tubing approximately 1" in length and weighing 2.1918 grams was placed in a rotating autoclave along with 21.8 grams of a sulfuric acid solution containing 5.2 wt. % sulfuric acid and 400.5 grams of water. The autoclave was sealed and heated to a temperature of about 200° C. The autoclave was maintained at a range of from 199° to 202° C. for a period of 10 hours. At the end of this period, heating was discontinued and the autoclave was allowed to return to room temperature. The pressure which had built up in the autoclave to 16 atmospheres was released and the autoclave was opened. The solution was recovered and it was found that the tube was completely corroded and dissolved, there being a 100% corrosion of said tube.

A repeat of the above experiment in which a similar piece of tubing weighing 2.4584 grams was placed in an autoclave along with 150.2 grams of water and 8.3 grams of a sulfuric acid solution. The autoclave was again heated to 200° C., the steam pressure during the 10 hour period reaching 14 atmospheres. At the end of the 10 hour period, heating was discontinued and the pressure was discharged after the autoclave had returned to room temperature. Examination of the solution again determined that the tube was completely dissolved, there being a 100% corrosion of said tube.

EXAMPLE II

To illustrate the corrosion inhibiting properties of the metal salts of the present invention, a stainless steel 316 tube weighing 2.9776 grams was placed in a rocking autoclave along with 150 grams of water, 8.5 grams of sulfuric acid solution and 10.6 grams of a magnesium sulfate solution. The autoclave was sealed and heated to a temperature of 200° C., the autoclave being maintained at this temperature for a period of 10 hours during which time a steam pressure of 17 atmospheres was reached. At the end of the 10 hour period, heating was discontinued and, after the autoclave had reached room temperature, the excess pressure was discharged. The reaction mixture containing the tube was recovered from the autoclave and the tube was weighed. The weight of the tube at the conclusion of the experiment was 2.2029 grams, the weight loss corresponded to a 26% corrosion.

EXAMPLE III

To illustrate the ability of the co-catalyst system of the present invention to hydrate olefinic hydrocarbons with water, a catalyst system comprising 16.7 grams of a sulfuric acid solution and 21 grams of magnesium sulfate, along with 300 grams of water, were placed in a rotating autoclave. The autoclave was sealed and 22.65 grams of propylene were charged thereto. The autoclave was heated to a temperature of 202° C. and maintained thereat for a period of 1 hour, the operating pressure during this period reaching 38 atmospheres. Upon completion of the desired reaction time, heating was discontinued and, after the autoclave had returned to room temperature, the excess pressure was discharged. Analysis of the reaction mixture by gas chromatography showed that there had been a 50.7% conversion of the propylene with a 100 mole percent selectivity to isopropyl alcohol.

EXAMPLE IV

The above experiment may be repeated using another acidic compound such as nitric acid, hydrochloric acid, 12-tungstosilicic acid, trifluoromethanesulfonic acid and benzene sulfonic acid as a catalyst in conjunction with other corrosion-inhibiting metal salts such as barium chloride or beryllium nitrate to hydrate other olefins such as ethylene, n-butene, isobutene, and octene with water to form the corresponding alcohols such as ethyl alcohol, sec-butyl alcohol, tertbutyl alcohol and octyl alcohol.

We claim as our invention:

1. A process for the production of an alcohol which comprises hydrating an olefinic hydrocarbon at hydration conditions in the presence of an acidic compound selected from the group consisting of sulfuric acid, nitric acid, benzene sulfonic acid and trifluoromethane sulfonic acid and in the added presence of a corrosion inhibitor selected from the group consisting of nitrate, halide, carbonate and sulfate salts of magnesium, barium, beryllium and radium, and recovering the resultant alcohol.

2. The process as set forth in claim 1 in which said hydration conditions include a temperature in the range of from about 100° to about 300° C. and a pressure in the range of from about 1 to about 300 atmospheres.

3. The process as set forth in claim 1 in which said olefinic hydrocarbon contains from 2 to about 20 carbon atoms.

4. The process as set forth in claim 1 in which said inorganic compound is sulfuric acid.

5. The process as set forth in claim 1 in which said inorganic compound is nitric acid.

6. The process as set forth in claim 1 in which said acidic compound is benzene sulfonic acid.

7. The process as set forth in claim 1 in which said acidic compound is trifluoromethanesulfonic acid.

8. The process as set forth in claim 1 in which said corrosion inhibitor is magnesium sulfate.

9. The process as set forth in claim 1 in which said corrosion inhibitor is barium chloride.

10. The process as set forth in claim 1 in which said corrosion inhibitor is beryllium nitrate.

11. The process as set forth in claim 1 in which said olefinic hydrocarbon is propylene and said alcohol is isopropyl alcohol.

12. The process as set forth in claim 1 in which said olefinic hydrocarbon is n-butene and said alcohol is sec-butyl alcohol.

13. The process as set forth in claim 1 in which said olefinic hydrocarbon is octene and said alcohol is sec-octyl alcohol.

14. The process as set forth in claim 1 in which said olefinic hydrocarbon is isobutylene and said alcohol is tert-butyl alcohol.

15. The process as set forth in claim 1 in which said olefinic hydrocarbon is ethylene and said alcohol is ethyl alcohol.

* * * * *